(12) United States Patent
Carroux

(10) Patent No.: US 11,033,412 B2
(45) Date of Patent: Jun. 15, 2021

(54) SOLID WIRE URETERAL STENT

(71) Applicant: Gyrus ACMI, Inc., Southborough, MA (US)

(72) Inventor: Alexander Carroux, Waltham, MA (US)

(73) Assignee: Gyrus Acmi, Inc., Westborough, MA (US)

(*) Notice: Subject to any disclaimer, the term of this patent is extended or adjusted under 35 U.S.C. 154(b) by 41 days.

(21) Appl. No.: 15/235,245

(22) Filed: Aug. 12, 2016

(65) Prior Publication Data
US 2018/0042741 A1  Feb. 15, 2018

(51) Int. Cl.
A61F 2/94 (2013.01)
A61M 27/00 (2006.01)
A61M 25/01 (2006.01)
A61F 2/844 (2013.01)
A61F 2/962 (2013.01)
A61F 2/848 (2013.01)

(52) U.S. Cl.
CPC .............. A61F 2/94 (2013.01); A61F 2/844 (2013.01); A61F 2/962 (2013.01); A61M 25/01 (2013.01); A61M 27/008 (2013.01); A61F 2002/8486 (2013.01); A61F 2210/0014 (2013.01); A61F 2220/0008 (2013.01)

(58) Field of Classification Search
CPC ..... A61F 2002/048; A61F 2/962; A61F 2/966
USPC ............................................ 623/23.65–23.7
See application file for complete search history.

(56) References Cited

U.S. PATENT DOCUMENTS

| 4,713,049 A | 12/1987 | Carter .................. 604/8 |
| 5,295,954 A | 3/1994 | Sachse ................ 604/8 |
| 5,647,843 A | 7/1997 | Mesrobian et al. ........... 604/8 |
| 5,681,274 A | 10/1997 | Perkins et al. ............ 604/8 |
| 5,791,036 A * | 8/1998 | Goodin ............. A61M 25/0014 29/423 |
| 6,395,021 B1 | 5/2002 | Hart et al. .............. 623/1.15 |
| 6,569,150 B2 | 5/2003 | Teague et al. ............... 604/524 |
| 6,887,215 B2 | 5/2005 | McWeeney .................. 604/9 |
| 7,169,139 B2 | 1/2007 | Teague et al. .............. 604/524 |
| 7,972,292 B2 | 7/2011 | Behl et al. .................. 604/8 |
| 8,512,272 B2 | 8/2013 | Ostrovsky et al. ................ 604/8 |
| 2003/0130683 A1* | 7/2003 | Andreas .................. A61F 2/88 606/200 |

(Continued)

FOREIGN PATENT DOCUMENTS

| EP | 0789602 A1 | 8/1997 |
| EP | 3281668 A1 | 2/2018 |

OTHER PUBLICATIONS

"Resonance Metallic Ureteral Stent", Cook Medical, 2014, www.cookmedical.com, 2 pgs.

(Continued)

Primary Examiner — Yashita Sharma
(74) Attorney, Agent, or Firm — Schwegman Lundberg & Woessner, P.A.

(57) ABSTRACT

Disclosed herein is an apparatus. The apparatus includes a solid wire and a delivery catheter. The solid wire being provided with one or more retention mechanisms at a proximal end, a distal end, or both. The delivery catheter being capable of maintaining the one or more retention mechanisms in a delivery configuration. The one or more retention mechanisms are configured to expand to a deployed configuration upon removal of the delivery catheter.

19 Claims, 2 Drawing Sheets

(56) References Cited

U.S. PATENT DOCUMENTS

| | | | |
|---|---|---|---|
| 2003/0191450 A1 | 10/2003 | Teague et al. | 604/524 |
| 2004/0138644 A1* | 7/2004 | DiCarlo | A61L 29/085 |
| | | | 604/524 |
| 2004/0193092 A1 | 9/2004 | Deal | 604/8 |
| 2005/0240141 A1 | 10/2005 | Aliski et al. | 604/8 |
| 2005/0240278 A1 | 10/2005 | Aliski et al. | 623/23.7 |
| 2007/0032880 A1* | 2/2007 | Maeda | A61M 27/008 |
| | | | 623/23.7 |
| 2011/0172678 A1 | 7/2011 | Behl et al. | 606/127 |
| 2011/0230950 A1 | 9/2011 | Knapp | 623/1.11 |
| 2011/0320008 A1* | 12/2011 | Teague | A61M 27/008 |
| | | | 623/23.65 |
| 2013/0173016 A1 | 7/2013 | Devereux | 623/23.66 |
| 2014/0172118 A1 | 6/2014 | Pendleton et al. | 623/23.66 |
| 2017/0202688 A1* | 7/2017 | Caldwell | A61F 2/04 |

OTHER PUBLICATIONS

"European Application Serial No. 17179427.4, Extended European Search Report dated Nov. 16, 2018", 7 pgs.

"European Application Serial No. 17179427.4, Response filed Aug. 3, 2018 to Extended European Search Report dated Jan. 16, 2018", 17 pgs.

\* cited by examiner

SOLID WIRE URETERAL STENT

BACKGROUND

Field of the Invention

The invention relates to an apparatus and method for stenting a passageway of a human or animal body, and more specifically relates to an apparatus and method for a ureteral stent.

Brief Description of Prior Developments

A ureter is a tubular passageway in the body that conveys urine from a kidney to a bladder. Ureteral stents are used to facilitate urinary drainage from the kidney to the bladder in patients have a ureteral obstruction or injury, or to protect the integrity of the ureter in a variety of surgical manipulations. Ureteral stents are typically about 30 cm long, hollow catheter-like devices made from a polymer and placed within the ureter with the distal end residing in the kidney and the proximal end residing in the bladder. One or both ends of a ureteral stent may be coiled in a pigtail shape to prevent the upward and/or downward migration of the stent due to patient movement. For example, the ureter may stretch up to 5 cm in either direction during a patient's normal bodily movements, such as movement during breathing. If the stent is not sufficiently anchored, this may result in stent migration and displacement.

Ureteral stents are placed in a ureter to support opening of the passageway of the ureter between the kidney and the bladder to promote the flow path of urine. Traditional ureteral stents may be formed of an outer plastic material surrounding an inner lumen. Urine may be encouraged to flow down from the kidney to the bladder partially via the inner lumen and partially around the outside of the stent in the space between the stent and the ureter. It has been shown that a majority of flow created by the stent may be between the outer lumen of the ureteral stent and the inner wall of the ureter.

The Cook Resonance ureteral stent, for example, uses a coiled nitinol tube as a ureteral stent and which is provided with pigtail coils on both the distal kidney end and proximal bladder end for maintaining positioning in a patient.

It would be desirable to have a ureteral stent that was a thin wire so that in the event a benign or metastatic obstruction was present in the ureter, there would be relatively low difficulty in getting the stent to push past the obstruction due to the relatively small diameter and high column strength. It would also be desirable to have a ureteral stent that was capable of being delivered via small delivery member configured for increased patient comfort.

SUMMARY

In accordance with one aspect of the invention, an apparatus is disclosed. The apparatus includes a solid wire and a delivery catheter. The solid wire being provided with one or more retention mechanisms at a proximal end, a distal end, or both. The delivery catheter being capable of maintaining the one or more retention mechanisms in a delivery configuration. The one or more retention mechanisms are configured to expand to a deployed configuration upon removal of the delivery catheter.

In accordance with another aspect of the invention, a method is disclosed. A delivery catheter is provided. A solid wire is inserted into the delivery catheter. The solid wire includes one or more retention mechanisms at a proximal end, a distal end, or both. The delivery catheter is configured to maintain the one or more retention mechanisms in a delivery configuration.

BRIEF DESCRIPTION OF THE DRAWINGS

The foregoing aspects and other features of the invention are explained in the following description, taken in connection with the accompanying drawings, wherein.

DETAILED DESCRIPTION

Figure 1:
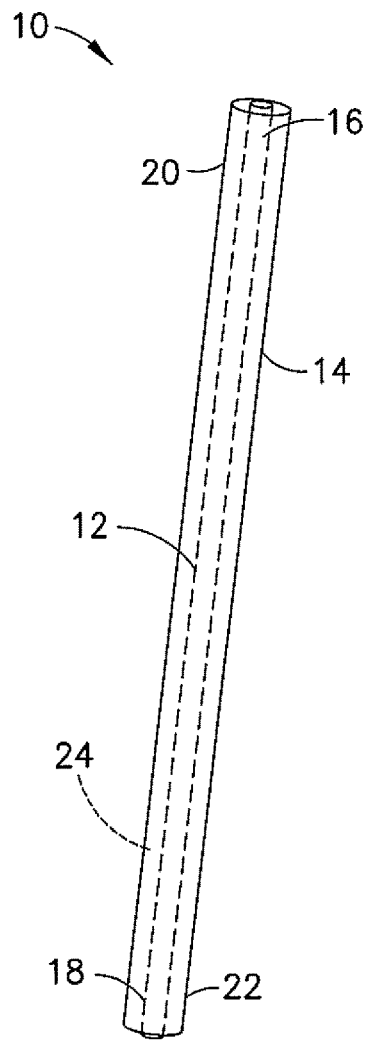
FIG. 1 is a perspective view of a ureteral stent (in a delivery configuration) incorporating features of the invention.

Referring to FIG. 1, there is shown a perspective view of a ureteral stent 10 incorporating features of the invention. Although the invention will be described with reference to the exemplary embodiments shown in the drawings, it should be understood that the invention can be embodied in many alternate forms of embodiments. In addition, any suitable size, shape or type of elements or materials could be used.

The ureteral stent 10 comprises a wire 12 and a delivery catheter 14. The wire 12 comprises a distal end 16 and an opposite proximal end 18. The delivery catheter comprises a first end 20 and an opposite second end 22. The configuration shown in FIG. 1 illustrates the ureteral stent in a delivery configuration wherein the distal end 16 of the wire 12 is substantially aligned with the first end 20 of the catheter 14 and the proximal end 18 of the wire 12 is substantially aligned with the second end of the catheter 14.

The wire 12 comprises a solid wire formed from a shape-memory alloy such as nitinol, for example. However, in alternate embodiments any suitable shape-memory alloy may be provided. The wire 12 comprises any suitable diameter configured to fit within the delivery catheter 14.

The delivery catheter 14 comprises a general hollow tube shape. The catheter may comprise a size and shape of a 5 Fr. catheter (i.e. a catheter having a size five on the French scale or French gauge system). However, in alternate embodiments, any suitably sized catheter may be provided. According to various exemplary embodiments, the delivery catheter 14 comprises a metal support structure 24 configured to rigidly support the delivery catheter in maintaining a straight configuration of the solid nitinol wire 12 during delivery of the stent. The metal support structure may include a coil braid which is woven within a polymer layer. However, in alternate embodiments, any suitable support structure may be provided.

As mentioned above, in the delivery configuration shown in FIG. 1 the ends 16, 20 are substantially aligned and the ends 18, 22 are substantially aligned such that the catheter 14 surrounds the wire 12.

Figure 2:
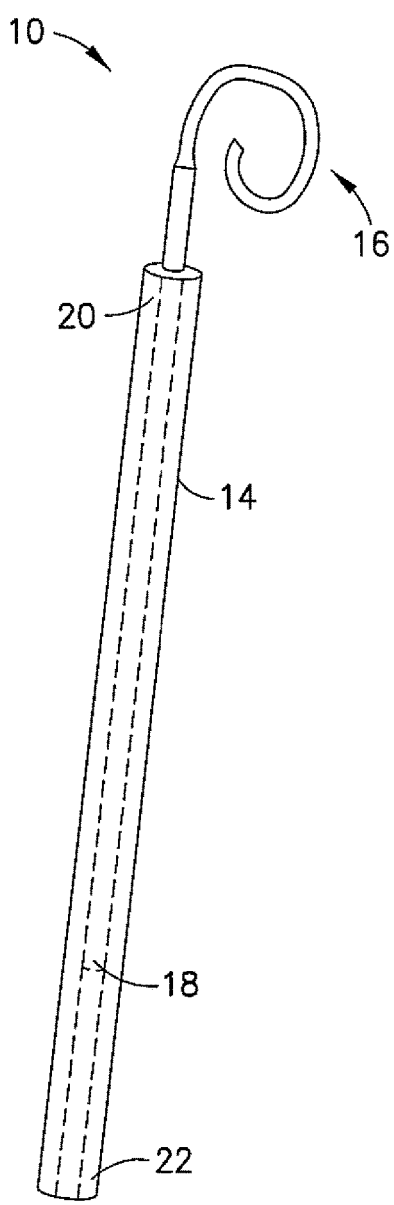
FIG. 2 is a perspective view of the ureteral stent shown in FIG. 1 in a transition from the delivery configuration to a deployed configuration.

Referring now to FIG. 2, there is shown the wire 12 and catheter 14 in a transition from the delivery configuration to a deployed configuration. For example, FIG. 2 shows the catheter 14 slidably repositioned such that the first end 20 of the catheter 14 is moved in a direction towards the proximal end 18 of the wire. This provides for the distal end 16 of wire 12 to be exposed. With the distal end exposed (and no longer surrounded by the catheter which supports and maintains the wire in a straight configuration) the wire is configured to deform to a defined shape of the shape-memory alloy. In the embodiment shown in FIG. 2, the defined shape of the shape-memory alloy is a general curl or coil shape which is heat set at the distal end 16 of the wire 12. The general curl or coil shape provides a retention mechanism for the wire at the distal end 16.

Figure 3:
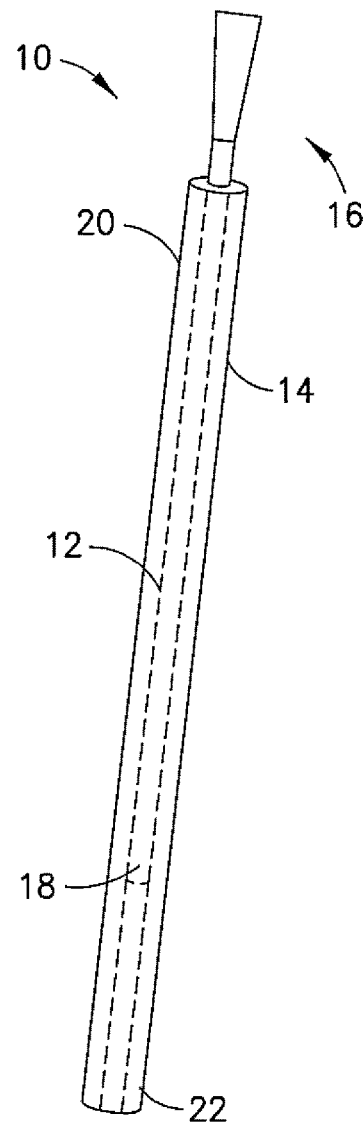
FIG. 3 is a perspective view of another example of a ureteral stent incorporating features of the invention.

It should be noted that although various exemplary embodiments have been described in connection with a general curl or coil shape as a retention mechanism, one skilled in the art will appreciate that the various exemplary embodiments are not necessarily so limited and that in alternate embodiments any suitable shape for a retention feature may be provided. For example, as shown in FIG. 3, a flared end or flared shape and a flattened tip may be provided as the retention mechanism. Additionally, in other embodiments, a long, thin, floppy tip shape may be provided.

Figure 4:
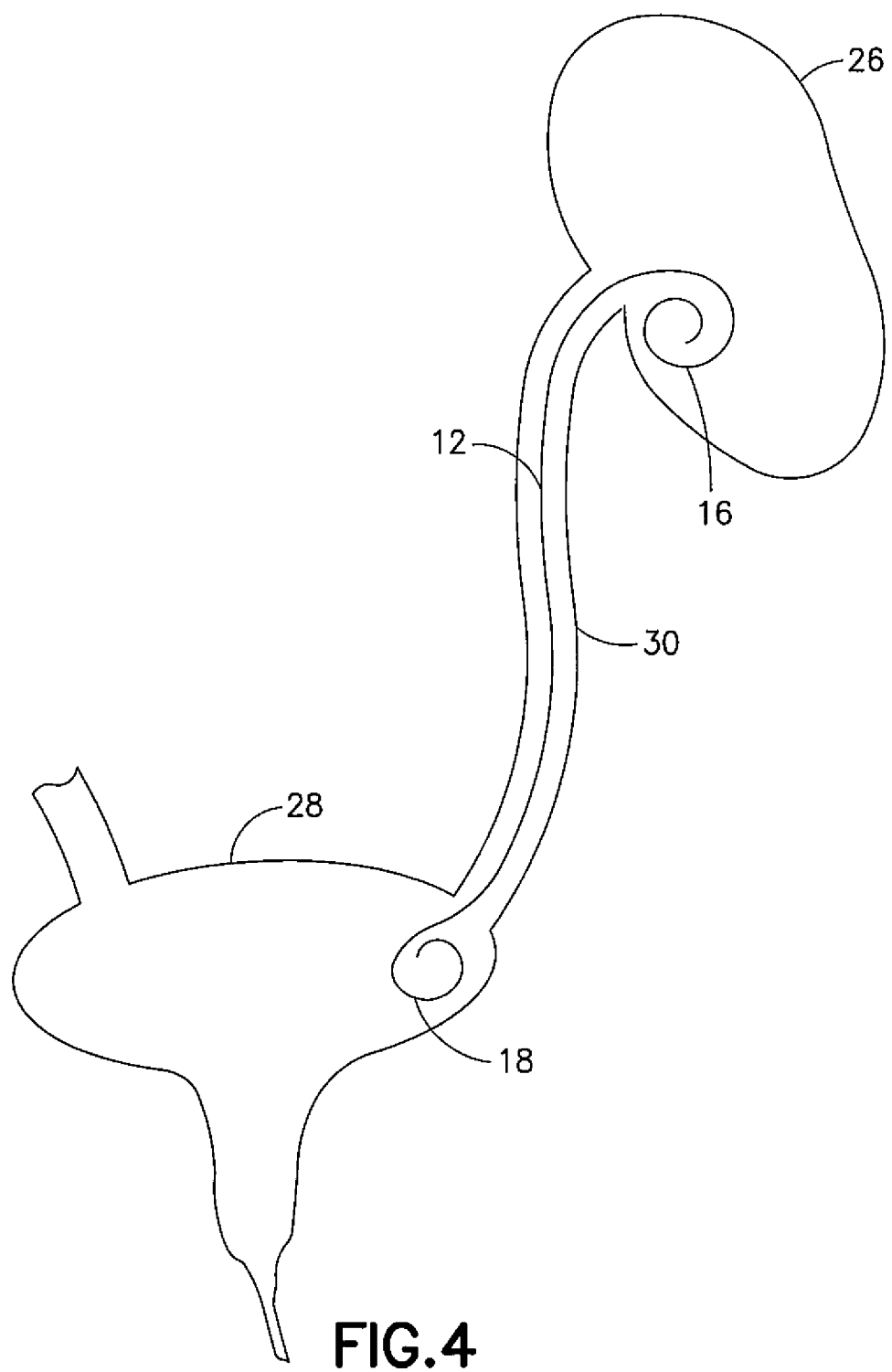
FIG. 4 is a perspective view of the ureteral stent shown in FIG. 1 deployed within a bladder, a ureter, and a kidney.

When the catheter 14 is fully removed from the wire 12, the other end of the wire is exposed to provide another retention mechanism at the proximal end 18 of the wire 12. This deployed configuration is shown in FIG. 4, wherein both the distal end and the proximal end of the wire comprise a general curl or coil shape as a retention mechanism. However, it should be noted that in alternate embodiments, different shapes could be provided at the distal and proximal ends.

As shown in FIG. 4, the stent 10 is provided as a catheter inserted wire. According to various exemplary embodiments, there would be no flow through the wire, however the flow around the wire would likely be considered sufficient. For example, urine may be encouraged to flow down from the kidney 26 to the bladder 28 around the outside of the wire 12 in the space between the wire and the ureter 30. Additionally, the wire would be locked in the kidney with a curl or spiral type structure (or retention mechanism) at the distal end 16, similar to a conventional stent. In the bladder, the wire could also be provided with a curl shaped structure or any other suitable shape at the proximal end 18 which would strive to reduce bladder irritation.

While various exemplary embodiments of the invention have been described in connection with the retention mechanisms mentioned above, one skilled in the art will appreciate that the various exemplary embodiments are not necessarily so limited and that other exemplary embodiments may include an expandable nitinol cage section. Additionally, it is contemplated that different output accessories can be used with the device of the present invention. In one embodiment, a lithotripsy shaft may be used in combination with a stone retrieval device (i.e. stone basket or stone grasper). Another embodiment might include a laser fiber used in combination with a stone retrieval device. Various other alternatives and configurations are possible to remove a calculus of interest and are herein incorporated by reference.

Technical effects of any one or more of the exemplary embodiments provide a stent made out of nitinol wire which would replace the traditional polymer stent. Instead of placing a tube structure over a guidewire, the present invention places a guidewire via a catheter (such as a 5 Fr catheter, for example). Various exemplary embodiments of the invention provide drainage for patients with both benign and malignant obstructions with good patient tolerance and without significant encrustation. Additionally, it has been shown that metallic stents can be maintained in situ for twelve months without significant encrustation.

Additional technical effects of any one or more of the exemplary embodiments provide for a nitinol wire provided with curls at a distal and proximal end to act as a ureteral stent, wherein a catheter is also provided for flattening the nitinol wire curls during placement of the stent. Many of the conventional configurations provide a lack of patient comfort, as even the smallest stents of 4.5 Fr represent a big structure in the ureter, stopping the natural peristaltic movement and allow for the reflux from the bladder through the ureteral orifice.

Below are provided further descriptions of various non-limiting, exemplary embodiments. The below-described exemplary embodiments may be practiced in conjunction with one or more other aspects or exemplary embodiments. That is, the exemplary embodiments of the invention, such as those described immediately below, may be implemented, practiced or utilized in any combination (e.g., any combination that is suitable, practicable and/or feasible) and are not limited only to those combinations described herein and/or included in the appended claims.

In one exemplary embodiment, a ureteral stent comprising: a solid wire, the solid wire being provided with one or more retention mechanisms at a proximal end, a distal end, or both; a delivery catheter, the delivery catheter being capable of maintaining the one or more retention mechanisms in a delivery configuration; wherein the one or more retention mechanisms are configured to expand to a deployed configuration upon removal of the delivery catheter.

A ureteral stent as above, wherein the solid wire comprises a shape-memory alloy.

A ureteral stent as above, wherein the solid wire comprises a solid nitinol wire.

A ureteral stent as above, wherein the solid wire is heat set to form the one or more retention mechanisms.

A ureteral stent as above, wherein the one or more retention mechanisms are curls at both the proximal end and the distal end.

A ureteral stent as above, wherein the one or more retention mechanisms include a curl at one end and a flared end at the other end.

A ureteral stent as above, wherein the delivery catheter is configured to surround the solid wire during insertion into an anatomical region of interest.

A ureteral stent as above, wherein the delivery catheter comprises a metal support structure configured to rigidly support the delivery catheter in maintaining a straight configuration of the solid nitinol wire during delivery.

A ureteral stent as above, wherein the metal support structure is a coil braid which is woven within a polymer layer.

In another exemplary embodiment, a method, comprising: providing a delivery catheter; and inserting a solid wire into the delivery catheter, wherein the solid wire comprises one or more retention mechanisms at a proximal end, a distal end, or both, and wherein the delivery catheter is configured to maintain the one or more retention mechanisms in a delivery configuration.

A method as above, wherein the one or more retention mechanisms are configured to deform to a deployed configuration upon removal of the delivery catheter.

A method as above, wherein the solid wire comprises a shape-memory alloy.

A method as above, wherein the solid wire comprises a solid nitinol wire.

A method as above, wherein the solid wire is heat set to form the one or more retention mechanisms.

A method as above, wherein the one or more retention mechanisms are curls at both the proximal end and the distal end.

It should be understood that components of the invention can be operationally coupled or connected and that any number or combination of intervening elements can exist (including no intervening elements). The connections can be direct or indirect and additionally there can merely be a functional relationship between components.

It should be understood that the foregoing description is only illustrative of the invention. Various alternatives and modifications can be devised by those skilled in the art without departing from the invention. Accordingly, the invention is intended to embrace all such alternatives, modifications and variances which fall within the scope of the appended claims.

What is claimed is:

1. A ureteral stent, comprising:
a solid wire having a first retention mechanism at a distal end, the solid wire comprising a general straight cylindrical shape along a majority of a length of the solid wire;
a delivery catheter configured to maintain the first retention mechanism in a delivery configuration;
wherein the first retention mechanism is configured to transition to a deployed configuration when the delivery catheter is removed from the solid wire, and wherein the solid wire is configured to provide a flow path between an outside diameter of the general cylindrical shape and an anatomical region of interest without another member therebetween, where the first retention mechanism comprises the solid wire having a flared shape and a flattened tip at the distal end, and where the first retention mechanism is configured to be inserted through a ureter into a kidney.

2. The ureteral stent of claim 1 wherein the solid wire comprises a shape-memory alloy.

3. The ureteral stent of claim 1 wherein the solid wire comprises a solid nitinol wire.

4. The ureteral stent of claim 1, wherein the solid wire is heat set to form the one or more retention mechanisms.

5. The ureteral stent of claim 1, wherein the delivery catheter is configured to surround the solid wire during insertion into the anatomical region of interest.

6. The ureteral stent of claim 1, wherein the delivery catheter comprises a metal support structure configured to rigidly support the delivery catheter in maintaining a straight configuration of the solid wire during delivery.

7. The ureteral stent of claim 6, wherein the metal support structure is a coil braid which is woven within a polymer layer.

8. The ureteral stent of claim 1 where the solid wire comprises a second retention mechanism at a proximal end, where at least one of the retention mechanisms comprises a non-curled shape.

9. The ureteral stent of claim 1 where the flared shape has a solid straight wire shape.

10. A ureteral stent comprising:
a solid wire comprising a proximal end and a distal end, where the solid wire comprises a first retention mechanism at the distal end, where the solid wire comprises a general cylindrical shape along a majority of a length of the solid wire; and
a delivery catheter on the solid wire, where the delivery catheter is configured to maintain the first retention mechanism at the distal end in a delivery configuration,
where the first retention mechanism is configured to transition from the delivery configuration to a deployed configuration when the delivery catheter is at least partially removed from the solid wire, where the solid wire is configured to provide a flow path between an outer side of the general cylindrical shape and an anatomical region of interest without another member therebetween, where the first retention mechanism at the distal end comprises the solid wire having a non-curled shape and a flattened tip at the distal end, and where the first retention mechanism is configured to be inserted through a ureter into a kidney.

11. The ureteral stent as in claim 10 where the non-curled shape comprises a flared shape which is straight along a centerline of the solid wire at the distal end.

12. The ureteral stent as in claim 10 where the solid wire is heat set to form at least one of the one or more retention mechanisms.

13. The ureteral stent as in claim 10 where the delivery catheter comprises a metal support structure configured to rigidly support the delivery catheter in maintaining a generally straight configuration of the solid wire in the delivery configuration.

14. The ureteral stent as in claim 13 where the metal support structure comprises a coil braid which is woven within a polymer layer.

15. The ureteral stent as in claim 10 where a proximal end of the solid wire comprises a curled shape.

16. A ureteral stent comprising:
a solid wire comprising a proximal end and a distal end, where the solid wire comprises a first retention mechanism at the distal end and a second retention mechanism at the proximal end; and
a delivery catheter configured to be located on the solid wire, where the delivery catheter is configured to maintain the first retention mechanism at the distal end and the second retention mechanism at the proximal end in a delivery configuration,
where the first retention mechanism at the distal end and the second retention mechanism at the proximal end are configured to transition from the delivery configuration to a deployed configuration when the delivery catheter is at least partially removed from the solid wire, where the solid wire is configured to provide a flow path between an outer lateral side of the solid wire and an anatomical region of interest without another member therebetween, where the first retention mechanism at the distal end comprises the solid wire having a flared straight solid wire shape at the distal end, and where the first retention mechanism is configured to be inserted through a ureter into a kidney.

17. The ureteral stent as in claim 16 where the flared shape comprises a non-curled shape.

18. The ureteral stent as in claim 16 where the proximal end of the solid wire has a curled shape.

19. The ureteral stent as in claim 16 where the flared straight solid wire shape comprises a flattened tip.

* * * * *